United States Patent [19]

Tanimoto

[11] Patent Number: 5,110,554
[45] Date of Patent: May 5, 1992

[54] COMBUSTION FURNACE FOR BURNING SAMPLE TO BE ANALYZED

[75] Inventor: Masahiro Tanimoto, Kyoto, Japan
[73] Assignee: Horiba, Ltd., Kyoto, Japan
[21] Appl. No.: 460,210
[22] Filed: Jan. 2, 1990

[30] Foreign Application Priority Data

Jan. 14, 1989 [JP] Japan .................. 1-2976[U]

[51] Int. Cl.⁵ .......................... G01N 31/12
[52] U.S. Cl. ........................... 422/78; 422/80; 432/72; 432/75; 432/241
[58] Field of Search .......... 422/78, 80; 432/72, 432/75, 241; 55/302, 498, 521

[56] References Cited

U.S. PATENT DOCUMENTS

| | | | |
|---|---|---|---|
| 3,972,682 | 8/1976 | Stephens et al. | 422/78 |
| 4,087,249 | 5/1978 | Okumoto et al. | 422/78 |
| 4,234,541 | 11/1980 | Bredeweg et al. | 422/78 |
| 4,816,228 | 3/1989 | Yoshida et al. | 422/78 |

Primary Examiner—Robert J. Warden
Assistant Examiner—Laura E. Collins
Attorney, Agent, or Firm—Price, Gess & Ubell

[57] ABSTRACT

A combustion furnace having a cylindrical filter arranged to pass gases between a combustion cylinder and a gas analyzer attached to an output port on the furnace. The gases to be analyzed are generated from a sample burned in the combustion cylinder and removed through the filter. A cleaning gas supply port and supply line for supplying a cleaning gas to the inside of the furnace are provided. The cleaning gas is under pressure and may be oscillated to assist in the removal of dust stuck to the filter and the interior of the furnace. The improved dust removal provides for a much cleaner furnace and a more accurate analysis of the sample.

4 Claims, 3 Drawing Sheets

PRIOR ART

COMBUSTION FURNACE FOR BURNING SAMPLE TO BE ANALYZED

BACKGROUND OF THE INVENTION

1. Field of the Invention

The present invention relates to a combustion furnace for burning a sample to be analyzed.

2. Description of Related Art

It is well known that a sample can be analyzed by burning the sample in a furnace and analyzing the gaseous ingredients emitted. It is also well known that the combustion of the sample generates a large amount of dust. Cylindrical filters have been tried for removal of this residual dust. However, the dust generated by combustion still remains a problem. Additionally, burning agents such as tungsten and tin, which may be added to promote the extraction of ingredients from the sample, increase the quantity of dust generated.

The quantity of dust generated by combustion of the sample creates problems in the system. The dust sticks to the filter, as well as to the internal areas of the combustion chamber, creating problems in that the filtration effect of the filter is lowered. Moreover, the extracted ingredients to be analyzed are adsorbed by the dust, thus lowering the accuracy of the analysis.

Accordingly, combustion furnaces for the burning of samples have been provided with a device for removing the dust stuck to inner surfaces of the filter and the furnace, as shown in FIG. 3.

FIG. 3 shows a conventional furnace for analyzing the ingredients of a sample. The furnace has a body 31 and a combustion cylinder 32 provided in the body 31. A heater 33 used for high-frequency heating is located on the periphery of a combustion cylinder 32. A crucible 34, which contains a sample to be analyzed, is placed on a holding member 35. A cylindrical filter 36 is arranged in a manner that permits the ingredients to be analyzed to travel from the combustion cylinder 32 to the outlet port 39. A cleaning rod 37 is provided that reciprocally slides and rotates in a circumferential direction within the filter 36 and the combustion cylinder 32. The cleaning rod 37, which is also used as a lance, is provided with a brush 38 mounted on an end for cleaning inner surfaces of the filter 36 and the combustion cylinder 32. A heating member 40 is provided for heating the filter 36.

In this prior art combustion furnace, the crucible 34, with the sample inside, is inserted into the combustion cylinder 32. The combustion cylinder 32 is heated by means of the heating member 33 to the point of burning the sample. The gaseous ingredients emitted are passed through the filter 36 and sent to an analyzer (not shown) through an outlet line (not shown) connected to the outlet port 39. The brush 38 is located in an upper portion inside the combustion cylinder 32 during the combustion of the sample. Dust generated by the combustion sticks to the inner surface of the combustion cylinder 32 and the filter 36.

The dust can then be removed by means of the brush 38 mounted on the end portion of the cleaning rod 37 by reciprocally sliding and rotating the cleaning rod 37 manually or by the use of a motive power (motor and the like).

The removal of the dust in the conventional combustion furnace, carried out by moving the brush 38 by means of the cleaning rod 37, presents problems. First, considerable labor is required. Second, the construction is complicated. Also, since only the inner circumferential surface of the filter 36 is scrubbed with the brush 38, it is difficult to remove the dust on an inside filament layer of filter 36. Thus, most probably part of the dust will not be removed by this method. Furthermore, since the surface of the filter 36 is varied by cleaning with the brush, repeated analysis of the waste ingredients is required.

An additional problem is presented by the fact that the brush 38 is always located within the combustion cylinder 32. This considerably complicates the construction of the interior of the furnace.

OBJECTS AND SUMMARY OF THE INVENTION

It is an object of the present invention to provide a combustion furnace that allows for removal of all the dust that is stuck to the filter and the interior of the furnace, while still retaining a simple structure.

A combustion furnace for burning a sample to be analyzed, having a cylindrical filter arranged so as to communicate gaseous ingredients between a combustion cylinder and the outlet port, is provided by a cleaning gas supply line which supplies the inside of the furnace with a cleaning gas through a gas port in the furnace body. The gas port is formed on the outer circumferential portion of the filter. Cleaning gas is sent to the inside of the furnace under pressure when it is necessary to remove dust from the filter and the interior regions of the furnace.

The gas port can also be used for removing the gas to be analyzed from the inside of the furnace. In this case, the cleaning gas supply line converts to a line for removing the gas to be analyzed by means of a switchover valve. In the alternative, the gas port for removing the gas to be analyzed and the gas port for supplying the cleaning gas can be separately provided.

With this combustion furnace, the sample is burned in the combustion cylinder. The gas to be analyzed is sent to an analyzer through the filter. The cleaning gas, such as $O_2$, for example, is sent into the body of the furnace under pressure through the cleaning gas supply line. It removes the dust that is stuck to the filter and the combustion cylinder. The cleaning gas is passed through the outside of the filter to the inside of the filter in order to separate the dust that is stuck to the filter and inner surfaces of the furnace. The pressure under which the cleaning gas is administered forces loose the dust particles stuck to the inside of the furnace. The cleaning gas may be continuously or intermittently applied. If the cleaning gas is applied intermittently by fluctuating the pressure of the gas, the dust-removing effect is improved.

DESCRIPTION OF THE PREFERRED EMBODIMENTS

The following description is provided to enable any person skilled in the furnace industry to make and use the invention, and sets forth the best modes contemplated by the inventor of carrying out his invention. Various modifications, however, will remain readily apparent to those skilled in the arts, since the generic principles of the present invention have been defined herein specifically to provide a relatively easily manufactured combustion furnace for use in analyzing samples.

The preferred embodiment of a combustion furnace for burning samples to be analyzed according to the present invention is described with reference to FIG. 1. In this preferred embodiment, a gas port or outlet part 5 for taking out the gas to be analyzed is also used for supplying a cleaning gas.

Figure 1:
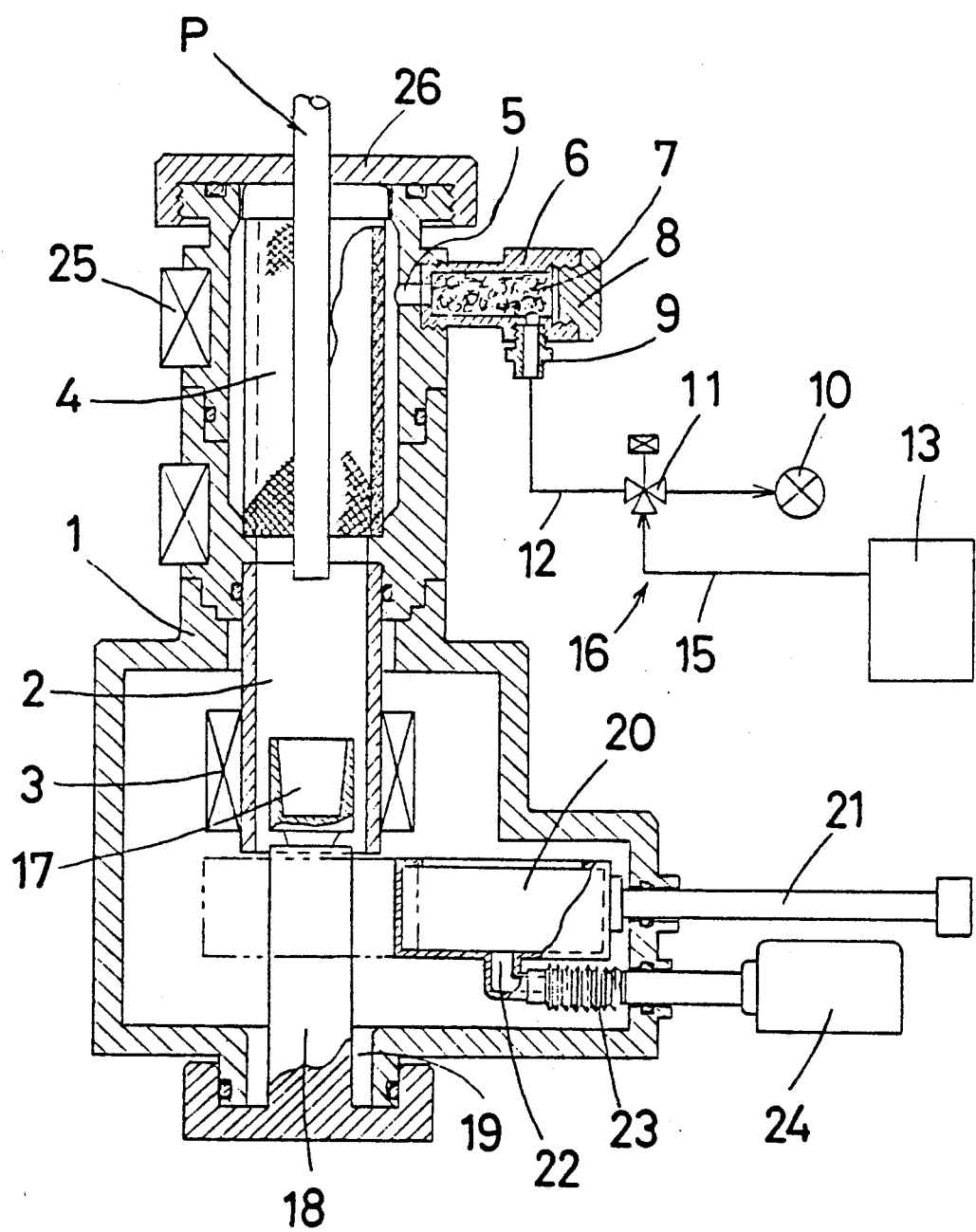
FIG. 1 is a sectional view showing a preferred embodiment of the present invention.

Referring now to FIG. 1, reference numeral 1 designates the body of a furnace having a combustion cylinder 2 provided within the body 1 of the furnace. A heating member 3 employing high-frequency heating is contained on an outer circumference of the combustion cylinder 2. A cylindrical filter 4 is disposed on a downstream side of the combustion cylinder 2 so that gases to be analyzed travel between the combustion cylinder 2 and an outlet port 5.

Outlet port 5 is formed on the body 1 of the furnace at an outer circumferential portion of the filter 4 to provide for the removal of the gas to be analyzed. A filter case 6, filled with quartz wool and the like, forms a subfilter 7. It is mounted on the body 1 of the furnace in order to communicate the gases to the outlet port 5. The filter case 6 has a cover 8. A connection pipe 9 is connected to the filter case 6 to allow the gas from the inside of the filter case 6 to flow to the analyzer 10 through a three-way valve 11 and pipe 12.

A cleaning-gas tank 13 of oxygen and the like, used for cleaning the filter 4, is connected with the three-way changeover valve 11 through a cleaning pipe 15 to create a cleaning-gas supply line 16.

A sample crucible 17 is mounted on an end of a holding member 18 and inserted into the combustion cylinder 2 through an inserting port 19 in the body 1 of the furnace. A dust-receptor 20 is disposed within the body 1 of the furnace for housing dust falling from the combustion cylinder 2. A guide rod 21 is fixedly mounted on the dust-receptor 20 at an end thereof and projects out of the body 1 of the furnace. This arrangement with the sliding of the guide rod 21 makes it possible for the dust-receptor 20 to be located below and on the side of combustion cylinder 2 during insertion of the crucible 17 into the combustion cylinder 2.

A dust-exhausting port 22 is formed on the bottom of the dust-receptor 20. A bellows-like flexible suction hose 23 is attached to the dust-exhausting port 22 and then connected to a suction device 24, such as a vacuum cleaner. The dust in receptor 20 may thus be taken out of the dust-receptor 20 by the suction device 24.

A heating member 25 is mounted on the body 1 of the furnace on a circumferential portion of the filter 4 for heating the filter 4. This prevents the gas to be analyzed from being adsorbed. Reference numeral 26 designates a cover for the body 1 of the furnace. P designates a lance passing through the cover 26 and through the center of filter 4.

Burning a sample in a combustion furnace having the above-described construction will now be described. The three-way changeover valve 11 is closed on the side of cleaning pipe 15. The holding member 18 is taken out of the body 1 of the furnace. A sample and any assistant combustion agent are placed in the crucible 17. The crucible 17 is inserted into the combustion cylinder 2. The heating member 3 is activated to heat and burn the sample. The gas generated from combustion of the sample passes through the filter 4 and the subfilter 6 into the analyzer 10 through the pipe 12.

After the combustion, in order to remove the dust stuck to an inner surface of the combustion cylinder 2 and the filter 4, the three-way changeover valve 11 is closed on the side of the analyzer 10. The crucible 17 is removed together with the holding member 18. The guide rod 21 is then adjusted, thereby positioning the dust-receptor 20 below the combustion cylinder 2, as shown by an imaginary line.

A cleaning gas from the cleaning-gas tank 13 is sent into the body 1 of the furnace under pressure through the cleaning pipe 15, the pipe 12, the subfilter 6, and the gas port 5.

Since the cleaning gas sent into the body 1 of the furnace is under pressure, dust stuck to the filter 4 is separated when the gas passes through the filter walls and enters the interior of the filter. The separated dust falls into the dust-receptor 20. The pressurized cleaning gas which has passed through the filter 4 also separates the dust that has stuck to the inner surface of the combustion cylinder 2 when it passes through the combustion cylinder 2. All the dust which has then been deposited in the dust-receptor 20 is then removed by the suction device 24 through the suction hose 23.

If the position of the three-way changeover valve 11 is fluctuated over a short time, for example, about 0.3 to 0.5 seconds, the fluctuation in the valve causes a resultant fluctuation in the pressure of the cleaning gas causing the filter 4 to vibrate, thereby more effectively separating dust that is stuck to the filter 4.

Since the cleaning gas is passed through the outside of the filter 4 to the inside of the filter 4, not only is the dust stuck to the surface removed, but the dust within the internal filament layers of the filter 4 is also removed.

Accordingly, the adsorption influence that the dust has on the gas to be analyzed is eliminated by the elimination of this internal filter dust.

Figure 2:
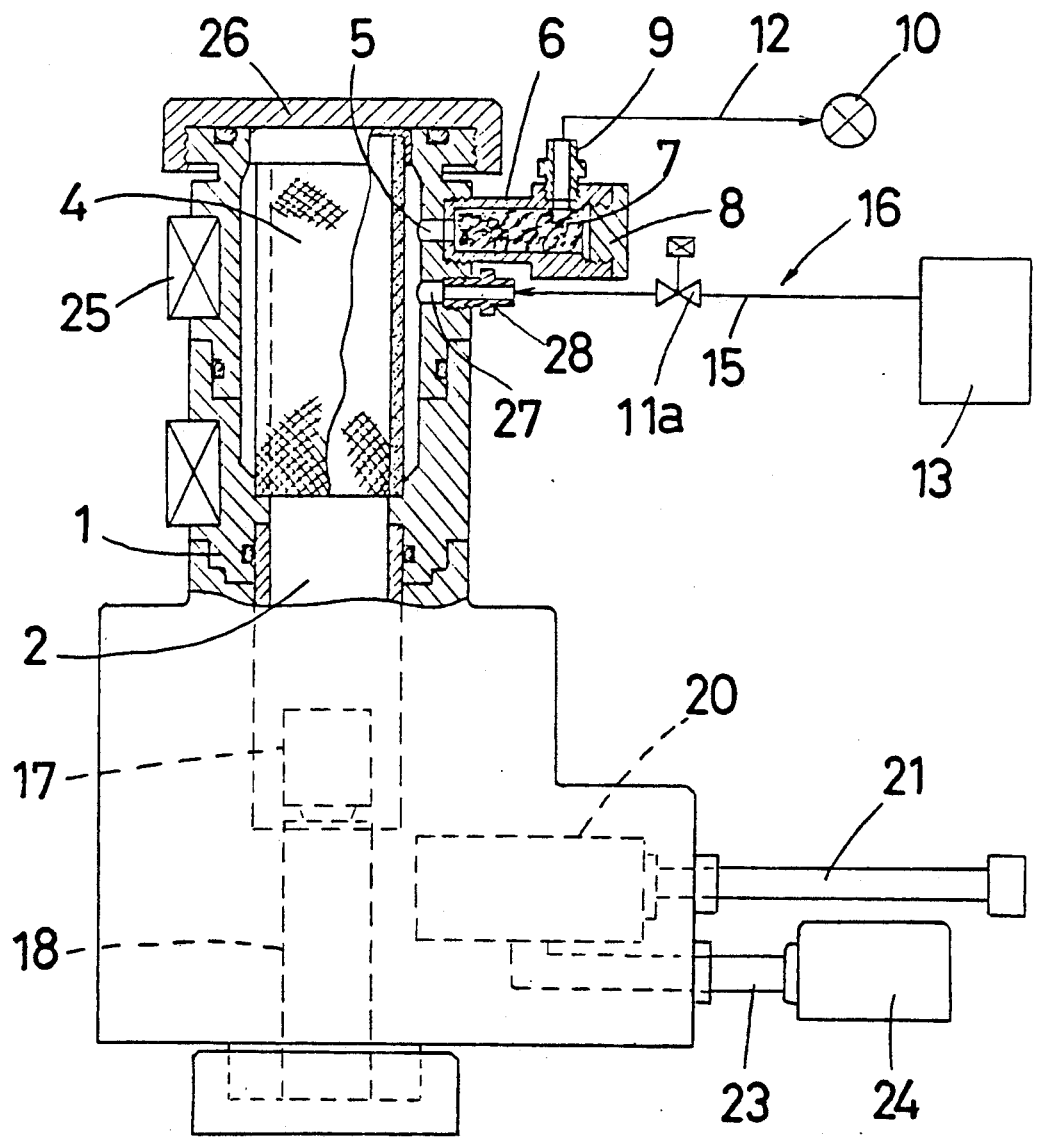
FIG. 2 is a partially sectioned front view showing another preferred embodiment of the present invention.
Figure 3:
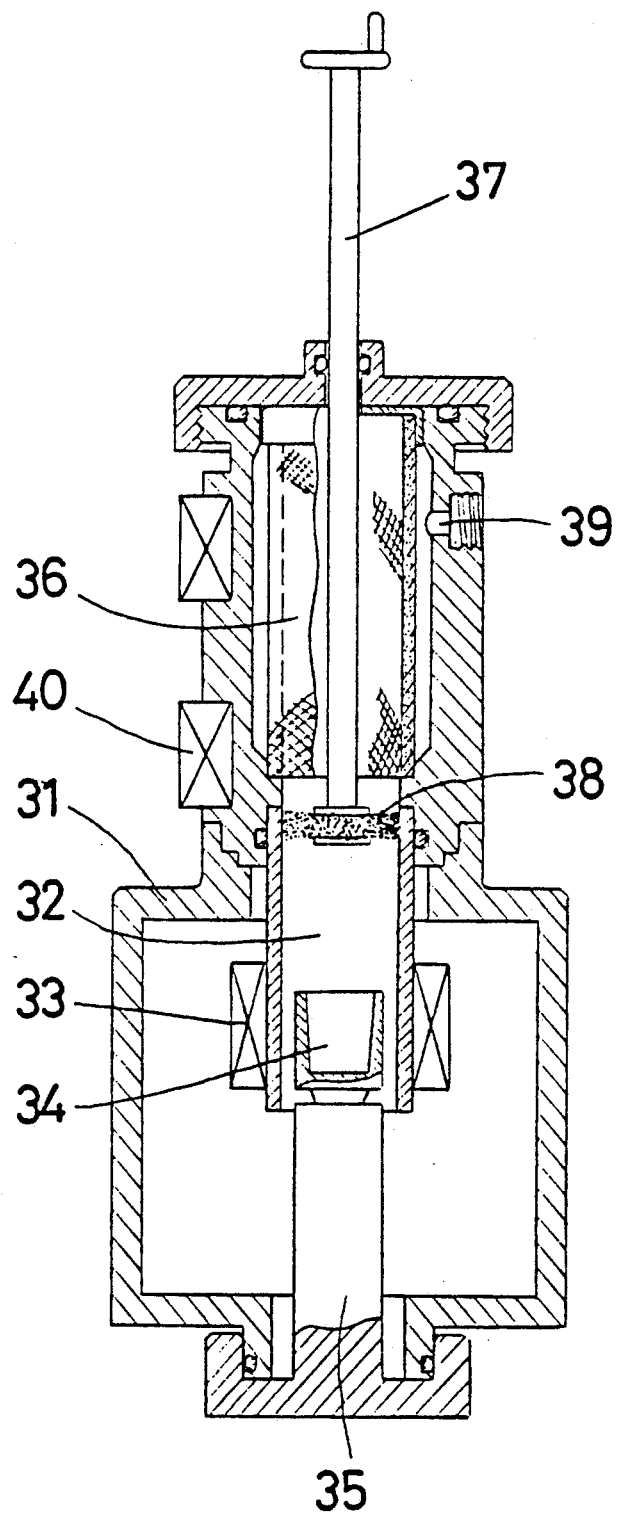
FIG. 3 is a sectional view showing a conventional prior art furnace.

FIG. 2 shows principal parts in another preferred embodiment. The, gas port 5 for taking out the gas to be analyzed and a gas port 27 for supplying the cleaning separately formed.

The gas port 27 is formed in the body 1 of the furnace for supplying the cleaning gas. A connection pipe 28 connects the gas port 27 with a cleaning gas tank 13 through a closing valve 11a and a cleaning pipe 15, to construct a cleaning gas supply line 16. An analyzer 10 is connected by a connection pipe 9 to a filter case 6 through a pipe 12.

Since the other structures are the same as in the preferred embodiment shown in FIG. 1, they are marked with the same reference numerals as in the preferred embodiment of FIG. 1.

In this second preferred embodiment, a gas to be analyzed is sent to the analyzer 10 from a gas port 5 through the pipe 12. To remove the dust stuck to a filter 4, a pump (not shown) is operated to send gas under pressure from the cleaning gas tank 13 to the inside of the body 1 of the furnace through the gas port 27. If a fluctuation of pressure in the cleaning gas supplied to the body 1 of the furnace is desired, this may be obtained by the repeated closing and opening of valve 11a.

According to the combustion furnace as described above in connection with FIG. 2, the cleaning gas is sent to the interior of the furnace under pressure through the gas port formed on the circumferential portion of the body of the furnace adjacent to the filter 4 when it is intended to remove the dust stuck to the cylindrical filter 4. The cleaning gas supplied to the body of the furnace is passed through the filter 4 from its outer circumferential area to its interior, thereby loosening the dust stuck to the filter and to the interior of the furnace.

In this way, not only is the dust stuck to the surface of the filter virtually completely removed, but the dust stuck to the internal filament layers of the filter is also removed. Thus, virtually all the dust stuck to the filter is removed. As a result, the accuracy of analysis is increased due to the virtual complete elimination of the dust. Adsorption of the gas to be analyzed by the dust left in the filter is thus prevented.

What is claimed is:

1. A combustion furnace system for burning a sample to be analyzed, consisting of:
   a furnace body;
   a combustion cylinder within the furnace body;
   a filter located inside said furnace body to pass gaseous substances from the combustion cylinder;
   a cleaning gas port on the furnace body at the outer circumference of the filter;
   a cleaning gas supply line attached to the cleaning gas port to send pressurized cleaning gas to the interior of the furnace body for the purpose of removing dust stuck to the interior of the furnace body and the filter;
   a three-way changeover valve on the outside of the furnace body, the three-way valve being repeatedly switched on and switched off while the cleaning gas is being sent to the interior of the furnace body to vary the pressure of the cleaning gas disbursed into the filter and interior of the furnace body; and
   an analyzer attached to the three-way valve so that the gas port may be used as an output port with gaseous residue from burned samples output to the analyzer through the gas port.

2. A combustion furnace system for burning a sample to be analyzed, comprising:
   a furnace;
   combustion chamber means within the furnace for holding a sample to be analyzed;
   analyzing means for analyzing a burnt sample;
   means for filtering gaseous substances from the combustion chamber means to the analyzing means;
   cleaning gas supply means for disbursing pressurized gas into the furnace;
   port means located proximal to the filter means for passing gaseous substances from the combustion chamber means to the analyzing means and for passing pressurized cleaning gas from the cleaning gas supply means to the furnace; and
   means for repeatedly fluctuating the pressure of the cleaning gas disbursed into the furnace for vibrating the filter means for the purpose of removing dust stuck to the interior of the furnace and in the filter means including a three-way changeover valve connected between the port means and the cleaning gas supply means that is repeatedly open and closed to vary the pressure of cleaning gas flowing therethrough.

3. A combustion furnace system for burning a sample to be analyzed, comprising:
   an analyzer for analyzing combustion gases;
   a combustion furnace body with a combustion cylinder;
   a filter arranged to communicate with the combustion cylinder through a gas port formed in the combustion furnace body, wherein a gas to be analyzed, generated from a sample burned in the combustion cylinder, is taken out through this filter;
   a cleaning gas supply line for supplying the inside of the combustion furnace body with a cleaning gas through the gas port formed in the body of the furnace at an outer circumferential portion of said filter, said cleaning gas being sent into the body of the furnace under pressure to remove dust stuck to the filter, and
   means for repetitively varying the cleaning gas pressure supplied to the supply line, including a three-way changeover valve connected to the gas port, said valve being repeatedly opened and closed while cleaning gas is being forced therethrough, said analyzer and said cleaning gas supply line being connected with said three-way changeover valve.

4. A combustion furnace for burning a sample to be analyzed comprising:
   a furnace body;
   a combustion cylinder in the furnace body;
   a cylindrical filter located inside said furnace body to pass gaseous substances from the combustion cylinder;
   a cleaning gas supply port on the furnace body at the outer circumference of the filter;
   a cleaning gas supply line attached to the cleaning gas supply port to send pressurized cleaning gas to the interior of the furnace;
   means for repetitively varying the cleaning gas pressure supplied to the supply line, including a three-way changeover valve on the outside of the furnace body, and an analyzer attached to the three-way changeover valve, said cleaning gas supply line connected to said three-way changeover valve, and said cleaning gas supply port connected to said three-way changeover valve so that the gas supply port may be used as an output port for gaseous residues of burned samples to the analyzer.

* * * * *